United States Patent [19]

Kubota et al.

[11] Patent Number: 5,349,120
[45] Date of Patent: Sep. 20, 1994

[54] WHITE MUSHROOM

[75] Inventors: Noriyasu Kubota, Nagano; Yoshihiro Miyagawa, Iiyama; Yukita Kawano, Otsu, all of Japan

[73] Assignees: Takara Shuzo Co., Ltd., Kyoto; Nagano Prefectural Economic Federation of Agricultural Co-operatives, Nagano, both of Japan

[21] Appl. No.: 29,918

[22] Filed: Mar. 11, 1993

Related U.S. Application Data

[63] Continuation of Ser. No. 707,803, May 30, 1991, abandoned.

[30] Foreign Application Priority Data

Jul. 6, 1990 [JP] Japan ................... 2-177573

[51] Int. Cl.5 .................. A01H 15/00; A01G 1/04
[52] U.S. Cl. .................. 800/200; 800/DIG. 8; 47/1.1
[58] Field of Search ............ 800/200, DIG. 8; 47/1.1, 1.102

[56] References Cited

U.S. PATENT DOCUMENTS 4,940,837  7/1990  Kawano et al. .............. 800/200

FOREIGN PATENT DOCUMENTS 2109925  4/1990  Japan .............. A01H 15/00

*Primary Examiner*—David T. Fox
*Assistant Examiner*—E. F. McElwain
*Attorney, Agent, or Firm*—Wenderoth, Lind & Ponack

[57] ABSTRACT

A method for cultivation of *Lyophyllum ulmarium* to form a fruiting body. The *Lyophyllum ulmarium* is a strain capable of forming a white fruiting body with or without indistinct darker spots around the center thereof. Also provided is a strain of *Lyophyllum ulmarium* capable of forming such a white fruiting body.

6 Claims, No Drawings

WHITE MUSHROOM

This application is a continuation of now abandoned application, Ser. No. 07/707,803, filed on May 30, 1991.

BACKGROUND OF THE INVENTION

The present invention relates to a method for the artificial cultivation of white mushrooms and to a strain of white fruiting body.

*Lyophyllum ulmarium* is an edible mushroom of excellent flavor belonging to *Tricholomataceae, Tribus Lyophylleae, Lyophyllum* ["Genshoku Nihon Shinkinrui Zukan (I)" written by Imazeki and Hongo and published from Hoikusha (1987)].

As kinds of edible mushroom commonly used at present, there may be mentioned, *Lentinus edodes, Flammulina venutipes, Pleurotus ostreatus, Agricus biosporus* and *Lyophyllum ulmarium*, all of which are supplied in large quantities by artificial cultivation. Of these, most *Flammulina velutipes* placed in the market is white in color, and champignons are also white in color. Thus, white-colored mushrooms occupy a large part of commercially available edible mushrooms and are highly evaluated in the food market.

In nature, *Lyophyllum ulmarium* grows caespitose or singly on the dead or live wood of a variety of broad-leaved trees in autumn, and this mushroom has long been harvested for food because of its nice shape, crispy texture and excellent flavor. In recent years, artificial cultivation in a bottle or box using a sawdust-medium comprising rice bran has been established, which ensures steady harvest of *Lyophyllum ulmarium* throughout the year without regard to the season. In this sawdust-medium cultivation, primordia are formed after a "Kinkaki" operation ( an operation which promotes the formation of fruiting ) , and cultivation is continued until harvest of the fruit bodies can be done.

The present inventors formerly established this method for artificial cultivation of *Lyophyllum ulmarium* and provided a strain of *Lyophyllum ulmarium* suitable for the artificial cultivation [Japanese Patent Kokai No.273467/1988 (U.S. Pat. No.4940837)]. However, the cap color is all brown (though different in color shade) in the strains of *Lyophyllum ulmarium* distributed in nature and in the strain used for artificial cultivation, and no strain of *Lyophyllum ulmarium* having white caps is known. Thus, there has been a demand for the supply of mushroom with white fruiting body in the food market because of diversified cooking.

Under the above-described circumstances, the present invention is intended to provide a simple method for industrially producing white fruiting bodies of *Lyophyllum ulmarium* (mushroom of high edibility value), and to provide a strain of white fruiting body.

SUMMARY OF THE INVENTION

Briefly, the present invention relates to a method for cultivating mushroom with white fruiting body, which comprises inoculating a strain thereof onto a culture medium to form fruiting bodies. The present invention also relates to strains of *Lyophyllum ulmarium* with white fruiting body.

DETAILED DESCRIPTION OF THE INVENTION

As a result of intensive studies continued for a long time, the present inventors have established a method for the artificial cultivation of *Lyophyllum ulmarium*, and provided strains thereof suitable for artificial cultivation.

As strains of *Lyophyllum ulmarium* suitable for artificial cultivation, there may be mentioned, among others, *Lyophyllum ulmarium* M-8171 (FERM BP-1415), *Lyophyllum ulmarium* Lu 1-8 ( FERM BP-1416) and *Lyophyllum ulmarium* Lu 1-2.

The colors of the caps and stems of the fruiting bodies obtained by the artificial cultivation of these strains were as shown in Table 1 below.

TABLE 1

| Strains | Color of Fruiting Bodies | |
|---|---|---|
| | Cap | Stem |
| *Lyophyllum ulmarium* M-8171 | Light brown | Pale cream |
| *Lyophyllum ulmarium* Lu 1-8 | Light brown | Pale cream |
| *Lyophyllum ulmarium* Lu 1-2 | Dark brown | Cream |

Even with the strain that has been the closest to white, *Lyophyllum ulmarium* M-8171, its fruiting bodies have light brown caps. The present inventors discovered a fruiting body having a white cap and a white stem among fruiting bodies with caps and stems of the ordinary color of *Lyophyllum ulmarium* M-8171 being cultivated artificially for commercial use.

The present inventors isolated tissue from this white fruiting body, made an axenic culture on an agar medium, made a large-scaled cultivation with a sawdust medium to produce white fruiting bodies several times, and discovered that, by the use of this white mutant strain, mushrooms with white fruiting bodies having a color tone quite unknown at that time can be cultivated reproducibly. The present invention was accomplished on the basis of these findings.

The term "white" as used in this specification means a color close to white which results when the color of the caps of fruiting bodies of strains of *Lyophyllum ulmarium* is lightened. Therefore, said term a color ranging from pale cream to pure white.

The present invention will be explained below in more detail.

Any strain belonging to *Lyophyllum ulmarium* that is capable of producing white fruiting bodies may be used in this invention. For example, in Kijimadaira, Nagano Prefecture, a white fruiting body was discovered during artificial cultivation of *Lyophyllum ulmarium* M-8171, the white fruiting body was isolated, tissue culture was done, and the strain was designated *Lyophyllum ulmarium* KW-8171. Another example is the strain designated *Lyophyllum ulmarium* IW-8171, which was discovered in Iiyama, Nagoya Prefecture, and isolated in the same way. With the above-mentioned strains, white fruiting bodies were artificially cultivated by the method described in Japanese Kokai Patent Application No. 273467/1988 (U.S. Pat. No. 4,940,837). The colors of the caps and stems of the fruiting bodies obtained by this method were as shown in Table 2.

TABLE 2

| Strains | Color of Fruiting Bodies | |
|---|---|---|
| | Cap | Stem |
| *Lyophyllum ulmarium* IW-8171 | Pale cream | Pale cream |
| *Lyophyllum ulmarium* KW-8171 | White | White |

The color of the caps of the fruiting bodies obtained by the culture of *Lyophyllum ulmarium* IW-8171 is close to the color of the stems of the fruiting bodies of *Lyo-*

*phyllum ulmarium* M-8171, which has been the palest known up to now, and the whole fruiting bodies of *Lyophyllum ulmarium* IW-8171 look white. The fruiting bodies obtained by the cultivation of *Lyophyllum ulmarium* KW-8171 do not have any detectable color and look pure white.

The morphological characteristics of the fruiting body and spores of white strains *Lyophyllum ulmarium* KW-8171 and *Lyophyllum ulmarium* IW-8171 are as follows.

Shape: Fruiting body grows single but is usually densely caespitose. Cap is 5-15 cm in diameter and convex. Margin is round to elliptical. Surface is smooth and moist, without hairs. Color is white to pale cream with or without indistinct darker round spots on the center. Sometimes, the cap is cracked in the center when over-mature.

Tissue: Thick, dense, and with a gum-like smell. Tissue color is white.

Gills: White, broad, and adapted on the upper stripes.

Stripe: 3-7 cm long, 1-2 cm thick, attached eccentrically, and curved. Same color as cap. On upper part of the stripe, color is white with cottony or bloody appearance.

Sores: Almost round, smooth, colorless. 4.5-5.5×3-.5-4.5 µm, white spore print.

These characteristics agree with those of strain *Lyophyllum ulmarium* M-8171, except for color of fruiting bodies. These strains, *Lyophyllum ulmarium* KW-8171 and *Lyophyllum ulmarium* IW-8171, have been deposited at the Fermentation Research Institute, Agency of Industrial Science and Technology (1-3, Higashi 1-chome, Tsukuba City, Ibaragi Prefecture, Japan) under the accession number of FERM BP-3302 on June 21, 1990 and FERM BP-3303 on June 27, 1990, respectively.

Next, various properties of *Lyophyllum ulmarium* KW-8171 (FERM BP-3302 ) will be described below.

(1) Malt-extract agar culture (25° C.)

With 7 days' incubation, colonies were 42 mm in diameter and white with many aerial hyphae. At 10 days, colonies covered the entire surface of the medium. At 17 days, colonies were dense and white. Many aerial hyphae have grown on the surface of the colonies.

(2) Potato-glucose agar culture (25° C.)

With 7 days' incubation, colonies were 38 mm in diameter, dense, and white, with many aerial hyphae. At 10 days, colonies covered the entire surface of the medium. At 17 days, white hyphae had grown over the colonies.

(3) Czapek-Dox agar culture (25° C.)

With 7 days' incubation, colonies were 25 mm in diameter, with a few aerial hyphae. Density of colonies was very low. Mycelia had many ramifications. At 17 days, colonies covered the entire surface of the medium. They were white and thin. Mycelia had many ramifications.

(4 ) Sabouraud agar culture (25° C.)

With 7 days' incubation, colonies were 41 mm in diameter, white, and dense, with a cotton-like growth with many aerial hyphae. At 10 days, colonies covered the entire surface of the medium with a great number of aerial hyphae. Mycelia had ramifications. White and cottony.

(5) Oatmeal agar culture (25° C.)

With 7 days' incubation, colonies were 38 mm in diameter with a few aerial hyphae. Mycelia had many ramifications. At 10 days, colonies covered the entire surface of the medium with many cotton-like aerial hyphae. Whitish.

(6) Synthetic mucor agar culture (25° C.)

With 7 days' incubation, colonies were 23 mm in diameter, white, and had radiational growth. At 17 days, colonies covered the entire surface of the medium, with many cotton-like aerial hyphae.

(7 ) YpSs agar culture (25° C.)

With 7 days' incubation, colonies were 43 mm in diameter, white, and dense, with many mat-like aerial hyphae. At 10 days, colonies covered the entire surface of the medium with many aerial hyphae.

(8 ) Culture on Potato-glucose agar containing 0.5% garlic acid for detection of phenol oxidase (25° C.)

With 7 days' incubation, colonies were 20 mm in diameter, with mat-like growth, and white, with a few aerial hyphae. Ityphae had produced a brownish zone under themselves. The zone was 38 mm in diameter. At 17 days, colonies were 39 mm in diameter, and the brownish zone was 40 mm in diameter. New inocula grew twice as quickly as the old ones.

(9 ) Optimum temperature for the growth of mycelia

We inoculated a disk 5 mm in diameter, with mycelia that had grown on agar plate onto PGY agar medium plates. Then we cultured the plates at several different temperatures, and measured the diameter of each colony after 12 days' incubation. From the results, we estimated that the optimum temperature was around 25° C. The strain could not grow at 5° C. or 35° C.

(10) Optimum pH for the growth of mycelia

We inoculated mycelial chips grown on agar medium into PGY liquid medium (60 ml, without agar). Liquid medium was adjusted to several different pHs. We measured the dry weight of the roycelia after 15 days' incubation at 25° C. From the results, we estimated the optimum pH to be 7.0 to 8.0. This strain could grow at pH 3.5 to 10.0.

*Lyophyllum ulmarium* IW-8171 ( FERM BP-3303) showed the same mycological characteristics as *Lyophyllum ulmarium* KW-8171.

Next, to learn how to distinguish these strains, *Lyophyllum ulmarium* KW-8171 and *Lyophyllum ulmarium* IW-8171, from other strains of *Lyophyllum ulmarium*, we examined differentiation by sexual factors by dual culture on agar medium, based on the taxonomic finding that the hyphae of different strains are different from each other. The strains of *Lyophyllum ulmarium* examined were *Lyophyllum ulmarium* IFO 9637, *Lyophyllum ulmarium* IFO 30525, *Lyophyllum ulmarium* IFO 30775, *Lyophyllum ulmarium* Lu 1-8, *Lyophyllum ulmarium* Lu 1-17, *Lyophyllum ulmarium* Lu 1-2, *Lyophyllum ulmarium* M-8171, and three strains of *Lyophyllum ulmarium* purchased from supply companies for inocula. *Lyophyllum ulmarium* Lu 1-8 is a wild-type strain collected in the Daisen district of Tottori Prefecture, Japan, *Lyophyllum ulmarium* Lu 1-17 was collected in the Okushima district, Mie Prefecture, Japan, *Lyophyllum ulmarium* Lu 1-2 was collected in the Kiritsumi district of Gunma Prefecture, Japan. These strains were isolated in pure culture by the present inventors. *Lyophyllum ulmarium* M-8171 is the strain that was created by the mating of *Lyophyllum ulmarium* Lu 1-8 with *Lyophyllum ulmarium* Lu 1-17. The three strains purchased from the supply companies for inocula were strains of *Lyophyllum ulmarium* purchased from K.K. Kamiko Shukin Research Laboratories, Nippon Norin Shukin K.K., and Fujita Shokuyokin Reseach Laboratories. Dikaryons of each strain were excised from a stock culture (grew on PGY agar slant medium) as a block of 3 mm ×3 mm ×3 mm and both inoculated into a dikaryon block (same size) for strains *Lyophyllum ulmarium* KW-8171 or *Lyophyllum ulmarium* IW-8171. After incubation of the strain at 25° C. for 14 days, we judged whether an antagonistic line had formed at the interface between the colonies or not. The results are shown in Table 3 (+: antagonistic line was formed, —: no antagonistic line was formed).

TABLE 3

| | Antagonistic Line | |
|---|---|---|
| *Lyophyllum ulmarium* | *Lyophyllum ulmarium* KW-8171 | *Lyophyllum ulmarium* IW-8171 |
| IFO 9637 | + | + |
| IFO 30525 | + | + |
| IFO 30775 | + | + |
| Lu 1-8 | + | + |
| Lu 1-17 | + | + |
| Lu 1-2 | + | + |
| M-8171 | — | — |
| K.K. Kamiko Shukin Research Laboratories | + | + |
| Nippon Norin Shukin K.K. | + | + |
| Fujita Shokuyokin Research Laboratories | + | + |
| KW-8171 | — | — |
| IW-8171 | — | — |

As shown in Table 3, all known strains except for *Lyophyllum ulmarium* M-8171 formed an antagonistic line during dual culture with *Lyophyllum ulmarium* KW-8171 or *Lyophyllum ulmarium* IW-8171. From this result, the sexual factor of the strains *Lyophyllum ulmarium* KW-8171 and *Lyophyllum ulmarium* IW-8171 was found to be the same as that of the strain of *Lyophyllum ulmarium* M-8171. Moreover, other mycological characteristics of the strain *Lyophyllum ulmarium* KW-8171 and *Lyophyllum ulmarium* IW-8171 were close to the characteristics of strain *Lyophyllum ulmarium* M-8171. This suggested that strains *Lyophyllum ulmarium* KW-8171 and *Lyophyllum ulmarium* IW-8171 are the same strain as *Lyophyllum ulmarium* M-8171 except for the color of the fruiting bodies.

The strains of mushroom having white fruiting body of this invention can be cultured by the artificial methods commonly employed for the culture of *Flammulia velutipes, Pleurotus ostreatus* and *Lyophyllum ulmarium* (for example, bottle, bag and box cultivation).

*Lyophyllum ulmarium* KW-8171 and *Lyophyllum ulmarium* IW-8171 are typical examples of the *Lyophyllum ulmarium* strains with white fruiting body that can be used in the present invention, but any other strains having the characteristics described above those isolated from the nature and those prepared by mating, mutagenesis and gene manipulation may also-be used in the present invention.

EXAMPLES

Examples of the method of the present invention for artificially cultivating the strains of white fruiting body are described below, but these are not intended to limit the scope of the invention.

EXAMPLE 1

*Lyophyllum ulmarium* IW-8171 (FERM BP-3303) was inoculated onto 100 ml of a medium (pH 5.5) containing 2.0% glucose, 0.2% peptone, 0.2% yeast extract, 0.05% $KH_2PO_4$ and 0.05% $MgSO_4 \cdot 7H_2O$, and cultivation was continued at 25° C. for 10 days, giving liquid inoculum. Separately, 50 g of sawdust from a needle-leaved tree, 50 g of sawdust from a broad-leaved tree and 90 g of rice bran were thoroughly mixed together, and tap water was added to adjust the water content to 65%. The resulting mixture was press-bottled in a polypropylene, wide-mouthed bottle (volume: 850 ml), a hole of 1 cm diameter was made from the center of bottle mouth toward the bottom, and the bottle was stoppered with a cap. The culture medium was then autoclaved with steam at 120° C. for 60 minutes, and 20 ml of the liquid inoculum obtained above was inoculated onto the sterilized medium.

Incubation of the medium in dark at a temperature of 25° C. and a humidity of 50% for 25 days produced hyphae to fill of the bottle. The hyphae thus obtained were further cultured under the same conditions for 34 days to give fruiting bed. The upper layer of the fruiting bed was removed by a thickness of 1 cm (a "Kinkaki" operation), and 20 ml of tap water was added and allowed to be sufficiently absorbed. After removing the non-absorbed water, culture was performed for 9 days under 20-lux illumination at a temperature of 15° C. and a humidity of 90% to form a primordia. The culture was further continued for 14 days with the illuminance increased to 200 lux, thus giving white fruiting bodies. The caps and stems of the fruiting bodies thus obtained were both pale cream in color, and the whole fruiting bodies looked white. The yield of the white fruiting bodies was 115 g, and the taste was very nice.

EXAMPLE 2

*Lyophyllum ulmarium* KW-8171 (FERM BP-3302) was inoculated onto 100 ml of a medium (pH 5.5) containing 2.0% glucose, 0.2% peptone, 0.2% yeast extract, 0.05% $KH_2PO_4$ and 0.05% $MgSO_4 \cdot 7H_2O$, and cultivation was continued at 25° C. for 10 days, giving liquid inoculum. Separately, 50 g of sawdust from a needle-leaved tree, 50 g of sawdust from a broad-leaved tree and 90 g of rice bran were thoroughly mixed together, and tap water was added to adjust the water content to 65%. The resulting mixture was press-bottled in a polypropylene, wide-mouthed bottle (volume: 850 ml), a hole of 1 cm diameter was made from the center of bottle mouth toward the bottom, and the bottle was stoppered with a cap. The culture medium was then autoclaved with steam at 120° C. for 60 minutes, and 20 ml of tile liquid inoculum obtained above was inoculated onto the sterilized medium.

Incubation of the medium in the dark at a temperature of 25° C. and a humidity of 50% for 25 days produced hyphae to fill of the bottle. The hyphae thus obtained were further cultured under the same conditions for 34 days to give fruiting bed. The upper layer of the fruiting bed was removed by a thickness of 1 cm (a "Kinkaki" operation), and 20 ml of tap water was added and allowed to be sufficiently absorbed. After removing the non-absorbed water, culture was performed for 9 days under 20-lux illumination at a temperature of 15° C. and a humidity of 90% to form a primordia. The culture was further continued for 14 days with the illuminance increased to 200 lux, thus giving white fruiting bodies. The caps and stems of the fruiting bodies thus obtained were both white in color, the whole fruiting bodies looked pure white. The yield of the white fruiting bodies was 117 g, and the taste was very nice.

REFERENCE EXAMPLE 1

*Lyophyllum ulmarium* M-8171 (FERM BP-1415) was inoculated onto 100 ml of a medium (pH 5.5) containing 2.0% glucose, 0.2% peptone, 0.2% yeast extract, 0.05% $KH_2PO_4$ and 0.05% $MgSO_4 \cdot 7H_2O$, and cultivation was continued at 25° C. for 10 days, giving liquid inoculum. Separately, 50 g of sawdust from a needle-leaved tree, 50 g of sawdust from a broad-leaved tree and 90 g of rice bran were thoroughly mixed together, and tap water was added to adjust the water content to 65%. The resulting mixture was press-bottled in a polypropylene, wide-mouthed bottle (volume: 850 ml ), a hole of 1 cm diameter was made from the center of bottle mouth toward the bottom, and the bottle was stoppered with a cap. The culture medium was then autoclaved with steam at 120° C. for 60 minutes, and 20 ml of the liquid inoculum obtained above was inoculated onto the sterilized medium.

Incubation of the medium in the dark at a temperature of 25° C. and a humidity of 50% for 25 days produced hyphae to fill the bottle. The hyphae thus obtained were further cultured under the same conditions for 34 days to give fruiting bed. The upper layer of tile fruiting bed was removed by a thickness of 1 cm (a "Kinkaki" operation), and 20 ml of tap water was added and allowed to be sufficiently absorbed. After removing the non-absorbed water, culture was performed for 9 days under 20-lux illumination at a temperature of 15° C. and a humidity of 90% to form a primordia. The culture was further continued for 14 days with the illuminance increased to 200-lux, thus giving fruiting bodies. The caps and stems of the fruiting bodies thus obtained were light brown and pale cream in color, respectively, and the whole fruiting bodies looked light brown. The yield was 113 g, and the taste was very nice.

REFERENCE EXAMPLE 2

*Lyophyllum ulmarium* Lu 1–8 (FERM BP-1416) was inoculated onto 100 ml of a medium (pH 5.5) containing 2.0% glucose, 0.2% peptone, 0.2% yeast extract, 0.05% $KH_2PO_4$ and 0.05% $MgSO_4 \cdot 7H_2O$, and cultivation was continued at 25° C. for 10 clays, giving liquid inoculum. Separately, 50 g of sawdust from a needle-leaved tree, 50 g of sawdust from a broad-leaved tree and 90 g of rice bran were thoroughly mixed together, and tap water was added to adjust the water content to 65%. The resulting mixture was press-bottled in a polypropylene, wide-mouthed bottle (volume: 850 ml), a hole of 1 cm diameter was made from tile center of bottle mouth toward tile bottom, and the bottle was stoppered with a cap. The culture medium was then autoclaved with steam at 120° C. for 60 minutes, and 20 ml of the liquid inoculum obtained above was inoculated onto the sterilized medium.

Incubation of the medium in the dark at a temperature of 25° C. and a humidity of 50% for 25 days produced hyphae to fill the bottle. The hyphae thus obtained were further cultured under the same conditions for 66 days to give fruiting bed. The upper layer of the fruiting bed was removed by a thickness of 1 cm (a "Kinkaki" operation), and 20 ml of tap water was added and allowed to be sufficiently absorbed. After removing the non-absorbed water, culture was performed for 10 days under 20-lux illumination at a temperature of 15° C. and a humidity of 90% to form a primordia. The culture was furtiler continued for 13 days with the illuminance increased to 200-lux, thus giving fruiting bodies. The caps and stems of the fruiting bodies thus obtained were light brown and pale cream in color, respectively, and the whole fruiting bodies looked light brown. The yield was 112 g, and the taste was very nice.

The color of the fruiting bodies obtained in Example 1, Example 2, Reference Example 1 and Reference Example 2 is summarized in Table 4 below.

TABLE 4

|  | Cap Color | Stem Color | Color Tone of Whole Body |
|---|---|---|---|
| Example 1 | Pale cream | Pale cream | White |
| Example 2 | White | White | Pure white |
| Reference Example 1 | Light brown | Pale cream | Light brown |
| Reference Example 2 | Light brown | Pale cream | Light brown |

As is apparent from the foregoing, the present invention enables the production of white mushrooms highly valuable as food.

What we claim is:

1. A method for cultivation of mushrooms which comprises cultivating a *Lyophyllum ulmarium* strain selected from the group consisting of *Lyophyllum ulmarium* KW-8171 (FERM BP-3302) and *Lyophyllum ulmarium* IW-8171 (FERM BP-3303) on a suitable culture medium for cultivation to form a fruiting body.

2. A biologically pure culture of a strain belonging to *Lyophyllum ulmarium* selected from the group consisting of *Lyophyllum ulmarium* KW-8171 (FERM BP-3302) and *Lyophyllum ulmarium* IW-8171 (FERM BP-3303).

3. A method as claimed in claim 1, wherein said *Lyophyllum ulmarium* strain is *Lyophyllum ulmarium* KW-8171 (FERM BP-3302).

4. A method as claimed in claim 1, wherein said *Lyophyllum ulmarium* strain is *Lyophyllum ulmarium* IW-8171 (FERM BP-3303).

5. A biologically pure culture as claimed in claim 2, wherein said *Lyophyllum ulmarium* is *Lyophyllum ulmarium* KW-8171 (FERM BP-3302).

6. A biologically pure culture as claimed in claim 2, wherein said *Lyophyllum ulmarium* is *Lyophyllum ulmarium* IW-8171 (FERM BP-3303).

* * * * *